United States Patent
Granados

(10) Patent No.: US 6,755,776 B1
(45) Date of Patent: Jun. 29, 2004

(54) ANGIOPLASTY RADIATION THERAPY TO PREVENT RESTENOSIS

(76) Inventor: Louis Rogelio Granados, 9396 Richmond Ave. #520, Houston, TX (US) 77063

( * ) Notice: Subject to any disclaimer, the term of this patent is extended or adjusted under 35 U.S.C. 154(b) by 0 days.

(21) Appl. No.: 09/528,853

(22) Filed: Mar. 20, 2000

(51) Int. Cl.[7] .............................. A61N 5/00; B05D 3/00
(52) U.S. Cl. ........................................ 600/8; 427/2.12
(58) Field of Search .................. 600/1, 2, 4, 5, 600/6, 7, 8, 585, 433–435; 427/2.1–2.31

(56) References Cited

U.S. PATENT DOCUMENTS

| | | | | |
|---|---|---|---|---|
| 4,819,618 A | * | 4/1989 | Liprie | 600/7 |
| 5,141,487 A | * | 8/1992 | Liprie | 600/7 |
| 5,213,561 A | * | 5/1993 | Weinstein | 600/7 |
| 5,873,811 A | * | 2/1999 | Wang et al. | 600/5 |
| 6,132,677 A | * | 10/2000 | Ohriner | 419/67 |
| 6,149,574 A | * | 11/2000 | Trauthen et al. | 600/3 |
| 6,312,374 B1 | * | 11/2001 | Von Hoffmann | 600/3 |
| 6,458,069 B1 | * | 10/2002 | Tam et al. | 600/3 |

* cited by examiner

Primary Examiner—Charles Marmor
Assistant Examiner—David J. McCrosky
(74) Attorney, Agent, or Firm—Kenneth A. Roddy

(57) ABSTRACT

A radiation therapy apparatus and method for significantly reducing or preventing restenosis after angioplasty utilizes a stainless steel guide wire having a phosphorus beta emitting radiation source ionically bonded thereon at its distal end by a positive vapor deposition process. The radiation therapy wire is similar in size, shape, and flexibility to the conventional guide wire used for the angioplasty procedure, and is introduced using the same catheter to carry out the radiation therapy procedure. When the beta emitting source reaches the critical section in a vessel or artery, a protective sleeve is retracted and the radiation source is exposed to the damaged area for a sufficient amount of time for the vessel to absorb the required dosage. Because the range of beta radiation is much lower than gamma radiation, the risk of radiation damage to other areas is minimal. Since the half life of the P-32 is 14 days and the required absorbed dose should be at least 8 Gy, an initial activation of at least 14 mCi is recommended.

1 Claim, 1 Drawing Sheet

ANGIOPLASTY RADIATION THERAPY TO PREVENT RESTENOSIS

BACKGROUND OF THE INVENTION

1. Field of the Invention

This invention relates generally to angioplasty radiation therapy apparatus and methods, and more particularly to a surgical apparatus and method for reducing restenosis after angioplasty utilizing beta radiation and a catheter with a stainless steel guide wire having a beta emitting radiation source at the distal end.

2. Description of Prior Art

Restenosis is a type of wound in the process of healing and is the resultant of two components, artery constriction and internal hyperplasia. It has been proven that radiation can limit the hyperplasia component by killing the proliferating cells. The use of radioactive stents has shown effective results to eliminate or at least to reduce the intimal hyperplasia usually expressed as the ratio between the area of the artery to the fracture length.

The use of a stent with a gamma radiation source such as iridiuim-192 has been a first step in the development of a procedure to irradiate the area of the vessel under consideration. Typically, gamma sources using iridium-192 have been used to irradiate the arteries under a continuous or intermittent condition with different results. The source is implanted using a stent and the combination of the mechanical effect (stent is expanded using a balloon) together with the radiation level of the source, has been proven to be beneficial in reducing the restenosis as shown by angiography and ultrasound analysis. The rate of irradiation under which the vessel is targeted is very important since several experiments indicate that absorbed doses below 8 Grays may dramatically affect the results.

The use of a stent with a gamma radiation source may also present several problems. The stents carrying the radioactive source can create uncomfortable situations since they are designed to reside permanently in the area under treatment. The use of a gamma source has also proven to be not strong enough to deliver the minimum absorbed doses without affecting other organs because of its longer range.

Other known radioactive stent methods and apparatus involve the use of a seed-shaped radioisotope or "seed" mechanically attached to the guide wire or to the stent as the source of gamma or beta radiation.

The present invention is distinguished over the prior art, in general, by a radiation therapy apparatus and method for significantly reducing or preventing restenosis after angioplasty that utilizes beta radiation and a catheter with a stainless steel guide wire having a beta emitting radiation source at the distal end.

The present invention utilizes a physical vapor deposition process (PVD) to ionically bond a phosphorus target material directly to the surface of the guide wire to form a unitary structure without any mechanical joint or attachment in such a way that the wire itself will become the carrier and the holder of the source for the radiation therapy. The wire material to be coated is enclosed in a vacuum chamber where the temperature is raised. The deposition material (phosphorus) is vaporized by an electric arc. The phosphorus ions are mixed with a nitrogen gas to form a plasma. A negative charge is applied to the section of wire to be coated, and a high positive charge is applied to the plasma. These opposite charges of the plasma and the base material of the guide wire ionically bonds a firm and hard phosphorus film coating on the surface of the wire to form a unitary structure.

In this way the target (phosphorus) is bonded into the area of the guide wire which is then activated by neutrons using a high flux research reactor unit until the desired activation is reached.

The radiation therapy guide wire is similar in size, shape, and flexibility to the conventional guide wire used for the angioplasty procedure, and the cardiologist merely needs to remove the conventional guide wire after completion of the angioplasty procedure and introduce, using the same catheter, the radiation therapy wire of the present invention to carry out the radiation therapy procedure described herein.

In a preferred embodiment, the particular physical vapor deposition process (PVD) used to form the present radiation therapy wire is described in greater detail in a publication entitled *"Handbook of Physical Vapor Deposition Processing"*, by Donald M. Mattox, Noyes Publications, 1998 ISBN 0-8155-1422-0.

SUMMARY OF THE INVENTION

It is therefore an object of the present invention to provide a minimumly invasive radiation therapy procedure using a beta radiation source that will substantially reduce or prevent restenosis after balloon angioplasty and adds only approximately 20 minutes to the coronary angioplasty procedure.

It is another object of this invention to provide a radiation therapy guide wire having a beta emitting radiation source at the distal end formed by physical vapor deposition (PVD) that ionically bonds the beta radiation target material (phosphorus) to the base material of the wire to form a unitary structure and eliminates the need for a permanently activated stent and mechanical attachments or "seeds" having limited area/volume available for neutron activation.

Another object of this invention is to provide a radiation therapy guide wire having a beta emitting radiation source ionically bonded at the distal end by physical vapor deposition (PVD) that allows a cardiologist to reach smaller or angulated areas during a radiation therapy procedure.

Another object of this invention is to provide a radiation therapy guide wire having a beta emitting radiation source such as phosphorus-32 ionically bonded at the distal end that has a shorter energy range than gamma radiation thereby minimizing damage to other organs.

A further object of this invention is to provide a radiation therapy guide wire having a beta emitting radiation source such as phosphorus-32 ionically bonded at the distal end which is not restricted to the small area/volume of a seed, allows higher activation of the source, and allows it to exceed a minimum threshold of 8 Grays of absorbed dose to validate the procedure.

A still further object of this invention is to provide a radiation therapy guide wire having a beta emitting radiation source bonded at the distal end which does not utilize a seed and is sized to allow radiation therapy procedures using the same catheter delivery system that is used for the angioplasty procedure.

Other objects of the invention will become apparent from time to time throughout the specification and claims as hereinafter related.

The above noted objects and other objects of the invention are accomplished by a radiation therapy apparatus and method for significantly reducing or preventing restenosis after angioplasty which utilizes a stainless steel guide wire having a phosphorus beta emitting radiation source ionically bonded thereon at its distal end to form a unitary structure. The radiation therapy wire is similar in size, shape, and flexibility to the conventional guide wire used for the angioplasty procedure, and is introduced using the same catheter to carry lout the radiation therapy procedure. When the beta emitting source reaches the critical section in a vessel or artery, a protective sleeve is retracted and the radiation source is exposed to the damaged area for a sufficient amount of time for the vessel to absorb the required dosage. Because the range of beta radiation is much lower than gamma radiation, the risk of radiation damage to other areas is minimal. Since the half life of the P-32 is 14 days and the required absorbed dose should be at least 8 Gy, an initial activation of at least 14 mCi is recommended.

DESCRIPTION OF THE PREFERRED EMBODIMENT

Figure 1:
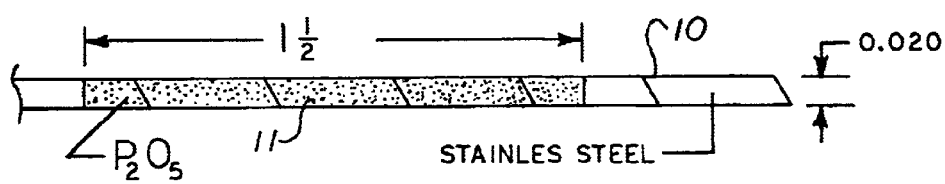
FIG. 1 is a side elevation of the distal end of a radiation therapy guide wire showing schematically a section with beta emitting phosphorus bonded thereto in accordance with the present invention.
Figure 2:
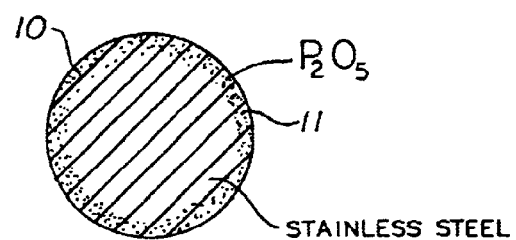
FIG. 2 is a transverse cross section through the radiation therapy guide wire with beta emitting phosphorus bonded thereto.

Referring now to FIGS. 1 and 2 there is shown, somewhat schematically, a radiation therapy guide wire 10 having a beta emitting radiation source 11 such as phosphorus-32 ionically bonded on a section thereof near its distal end. The radiation therapy wire 10 is formed of stainless steel sized to allow radiation therapy procedures using the same catheter delivery system that is used for the angioplasty procedure.

In the preferred embodiment the beta emitting radiation source utilized is phosphorus-32 (a pure beta emitter) with a half life of 14.28 days and a strength sufficient to provide minimum absorbed doses of from about 8–10 Grays (Gy). The target material such as phosphorus pentoxide (reagent) O5P2 (98% pure) or red phosphorus (99% pure) is ionically bonded to the surface of the stainless steel guide wire by a process known as physical vapor deposition (PVD).

The phosphorus target material is vaporized in a vacuum chamber by means of an electric arc. A negative charge is applied to the section of the wire to be coated. The phosphorus ions are mixed with nitrogen gas to form a plasma and a high positive charge is applied to the plasma. The highly charged positive ions of the phosphorus plasma are attracted to the negatively charged surface of the wire. This process assures perfect ion bonding between the phosphorus target material and the wire.

The area of the stainless steel wire having the phosphorus target material (phosphorus pentoxide or red phosphorus) bonded thereto is then activated in a nuclear reactor by bombarding it with a high flux of neutrons. Activation is monitored using a radiation dosimeter. After activation this portion of the wire is covered with a stainless steel sleeve to prevent any radiation to the medical personnel or to the patient.

The guide wire with the bonded beta emitting source is introduced to the area of the vessel where the balloon angioplasty was previously performed. When the beta emitting source reaches the critical section in the vessel, an interventional cardiologist retracts the protective sleeve covering the radiation source using differential pressure (vacuum). When the sleeve is removed the radiation source is exposed to the damaged area to allow the beta radiation to interact with the vessel (coronary artery) for about 3–5 minutes or sufficient time for the vessel to absorb the required dosage.

Because the present therapy guide wire does not utilize a seed radioisotope it can be introduced into the vessel using the same catheter delivery system that was used for the angioplasty procedure.

Since the range of beta radiation is much lower than gamma radiation, the risk of radiation damage to other areas is minimal. Energy distribution for beta radiation is exponential with distance, and it is estimated that the maximum range for beta radiation is about 8 mm in air. Since the half life of the P-32 is 14 days and the required absorbed dose should be at least 8 Gy, an initial activation of at least 14 mCi is recommended.

The apparatus may be provided as a packaged unit including the guide wire, radioactive source, and the activation monitoring dosimeter assembled in a portable case to be easily transported.

While this invention has been described fully and completely with special emphasis upon a preferred embodiment, it should be understood that within the scope of the appended claims the invention may be practiced otherwise than as specifically described herein.

What is claimed is:

1. A method of making a flexible radiation therapy wire for use in reducing restenosis by radiation at a site within a vascular structure following angioplasty, comprising the steps of:

providing an elongate flexible wire formed of stainless steel having a distal end;

placing at least the distal end of said stainless steel wire in a vacuum chamber;

vaporizing a phosphorus target material selected from the group consisting of phosphorus pentoxide and red phosphorus in said vacuum chamber by means of an electric arc;

applying a negative charge to a section of the distal end of the stainless steel wire;

introducing nitrogen gas into the vacuum chamber such that the phosphorus ions are mixed with nitrogen gas to form a plasma;

applying a high positive charge to the plasma such that highly charged positive ions of the phosphorus plasma are attracted to the negatively charged surface of the stainless steel wire to ionically bond the phosphorus target material into the surface of the stainless steel material and form a substantially unitary structure; and bombarding the area of the stainless steel wire having the ionically bonded phosphorus target material with a high flux of neutrons in a nuclear reactor.

* * * * *